(12) United States Patent
Vanatta (10) Patent No.: US 6,902,937 B2
(45) Date of Patent: Jun. 7, 2005

(54) METHOD FOR THE DETERMINATION OF LOW-CONCENTRATION ANIONS IN THE PRESENCE OF AN EXCESS OF ANOTHER ANION

(75) Inventor: Lynn E. Vanatta, Dallas, TX (US)

(73) Assignee: Air Liquide America, L.P., Houston, TX (US)

( * ) Notice: Subject to any disclaimer, the term of this patent is extended or adjusted under 35 U.S.C. 154(b) by 413 days.

(21) Appl. No.: 09/905,593

(22) Filed: Jul. 13, 2001

(65) Prior Publication Data

US 2003/0017611 A1 Jan. 23, 2003

(51) Int. Cl.[7] .............................................. G01N 31/00
(52) U.S. Cl. ...................... 436/101; 436/102; 436/100; 436/180; 436/171; 422/50; 422/68.1; 422/100
(58) Field of Search ................................ 422/105, 110, 422/114, 115, 81, 63, 103; 436/25, 52, 53, 180, 179, 120; 73/864.81, 863

(56) References Cited

U.S. PATENT DOCUMENTS

| | | |
|---|---|---|
| 3,626,178 A | 12/1971 | Cohen |
| 3,997,298 A | 12/1976 | McLafferty et al. |
| 4,055,987 A | 11/1977 | McFadden |
| 4,112,297 A | 9/1978 | Miyagi et al. |
| 4,160,161 A | 7/1979 | Horton |
| 4,242,097 A | 12/1980 | Rich, Jr. et al. |
| 4,265,634 A | 5/1981 | Pohl |
| 4,281,246 A | 7/1981 | White, V et al. |
| 4,314,823 A | 2/1982 | Rich, Jr. et al. |
| 4,455,233 A | 6/1984 | Pohl et al. |

(Continued)

FOREIGN PATENT DOCUMENTS

| | | |
|---|---|---|
| EP | 0 133 781 A1 | 3/1985 |
| EP | 0 133 782 A1 | 3/1985 |
| EP | 0 152 747 A2 | 8/1985 |
| EP | 0 180 321 B1 | 5/1986 |
| EP | 0 259 796 A3 | 3/1988 |

(Continued)

OTHER PUBLICATIONS

Weise, Wendy, "News Release—New Brochure Describes the Finnigan LCQ DUO Ion Trap Mass Spectrometer", http://www.thermoquest.com/pressroom/PR70.html, Thermo Quest Corporation, Dec. 11, 2000.

Dionex/Summit/AQA HPLCMS Product Introduction; Introducing the New Summit/AQA HPLC/MS; http://www.dionex.com/app/tree.taf?asset_id=68895, Dec. 11, 2000.

(Continued)

*Primary Examiner*—Jill Warden
*Assistant Examiner*—Sam P. Siefke
(74) *Attorney, Agent, or Firm*—Elwood L. Haynes (57) ABSTRACT

This invention relates to methods and apparatus for detecting, quantifying, and/or identifying trace quantities of an anion in the presence of an excess of another anion. One apparatus comprises a sample loop having a first end adapted to be connected to a sample-injection device and a second end adapted to be connected to an inlet of a first separator. An outlet of the first separator has connections to a first waste port and to an inlet of a first anion suppressor. An outlet of the first anion suppressor is connected to a first end of a concentrator and alternatively to waste, the concentrator connected at a second end to a second waste port and alternatively to a pump. The first end of the concentrator is alternatively connected to a second separator inlet, and the second separator is connected at an outlet thereof to an inlet of a second anion suppressor; and an outlet of the second anion suppressor is connected to a mass spectrometer.

12 Claims, 6 Drawing Sheets

U.S. PATENT DOCUMENTS

| | | | |
|---|---|---|---|
| 4,570,068 A | 2/1986 | Sakairi et al. | |
| 4,851,700 A | 7/1989 | Goodley | |
| 4,863,491 A | 9/1989 | Brandt et al. | |
| 4,867,947 A | 9/1989 | Andresen et al. | |
| 4,968,885 A | 11/1990 | Willoughby | |
| 4,980,057 A | 12/1990 | Dorn et al. | |
| 4,982,097 A | 1/1991 | Slivon et al. | |
| 4,999,098 A | 3/1991 | Pohl et al. | |
| 5,117,109 A | 5/1992 | Asakawa et al. | |
| 5,223,131 A | 6/1993 | Apffel, Jr. et al. | |
| 5,240,616 A | 8/1993 | Kato et al. | |
| 5,248,426 A | 9/1993 | Stillian et al. | |
| 5,266,192 A | 11/1993 | Ligon et al. | |
| 5,285,064 A | 2/1994 | Willoughby | |
| D347,396 S | 5/1994 | Ohnuma et al. | |
| 5,316,630 A | 5/1994 | Dasgupta | |
| 5,331,159 A | 7/1994 | Apffel, Jr. et al. | |
| 5,331,160 A | 7/1994 | Whitt | |
| 5,352,360 A | 10/1994 | Stillian et al. | |
| 5,368,727 A | 11/1994 | Takahashi et al. | |
| 5,447,553 A | 9/1995 | Apffel, Jr. et al. | |
| 5,468,452 A | 11/1995 | Hagiwara | |
| 5,569,365 A | 10/1996 | Rabin et al. | |
| 5,581,081 A | 12/1996 | Kato et al. | |
| 5,597,734 A | 1/1997 | Small et al. | |
| 5,773,615 A | 6/1998 | Small et al. | |
| 5,789,746 A | 8/1998 | Kato et al. | |
| 5,859,432 A | 1/1999 | Kato et al. | |
| 5,914,025 A | 6/1999 | Small | |
| 6,027,643 A | 2/2000 | Small et al. | |
| 6,077,434 A | 6/2000 | Srinivasan et al. | |
| 6,100,522 A | 8/2000 | Chiang | |
| 6,106,710 A | 8/2000 | Fischer et al. | |
| RE36,892 E | 10/2000 | Apffel, Jr. et al. | |
| 6,236,042 B1 | 5/2001 | Kato et al. | |
| 6,245,227 B1 | 6/2001 | Moon et al. | |
| 6,325,976 B1 | 12/2001 | Small et al. | |
| 6,706,527 B2 * | 3/2004 | Szecsody | 436/25 |

FOREIGN PATENT DOCUMENTS

| | | |
|---|---|---|
| EP | 0 259 796 A2 | 3/1988 |
| EP | 0 338 572 B1 | 10/1989 |
| EP | 0 338 572 A1 | 10/1989 |
| EP | 0 342 884 A1 | 11/1989 |
| EP | 0 343 972 A2 | 11/1989 |
| EP | 0 417 976 A2 | 3/1991 |
| EP | 0 417 976 A3 | 3/1991 |
| EP | 0 510 510 A3 | 10/1992 |
| EP | 0 510 510 A2 | 10/1992 |
| EP | 0 536 930 A1 | 4/1993 |
| EP | 0 555 962 A3 | 8/1993 |
| EP | 0 555 962 A2 | 8/1993 |
| EP | 0 646 239 B1 | 4/1995 |
| EP | 0 671 002 B1 | 9/1995 |
| EP | 0 758 449 B1 | 2/1997 |
| EP | 0 898 167 B1 | 2/1999 |
| EP | 0 898 167 A1 | 2/1999 |
| WO | WO 98/30314 A1 | 7/1998 |
| WO | WO 99/11351 A1 | 3/1999 |
| WO | WO 99/44054 A1 | 9/1999 |
| WO | WO 00/42426 A1 | 7/2000 |
| WO | WO 01/67090 A1 | 9/2001 |
| WO | WO 01/67091 A1 | 9/2001 |
| WO | WO 01/80283 A1 | 10/2001 |

OTHER PUBLICATIONS

Dionex, "The Use of Concentrator Columns in Ion Chromatography"; Technical Note 8, pp. 1–8, 1994.

Dionex, "Determination of Trace Anions in Concentrated Hydrofluoric Acid"; Technical Note 45, pp. 1–11, 1999.

Dionex, "Determination of Trace Anions in Concentrated Glycolic Acid"; Technical Note 46, pp. 1–11 1999.

Dionex, "Determination of Trace Anions in Concentrated Hydrofluoric Acid"; Application Note 78, 1994.

Dionex, "Determination of Trace Anions in Concentrated Bases Using AutoNeutralization Pretreatment/Ion Chromatography"; Application Note 93, Aug., 1994.

Dionex, "Determination of Trace Cations in Concentrated Acids Using AutoNeutralization Pretreatment/Ion Chromatography"; Application Note 94, Aug., 1994.

Small, Hamish, et al., "Novel Ion Exchange Chromatographic Method Using Conductimeric Detection", Analysis on Chemistry, vol. 47, No. 11, pp. 1801–1809, Sep. 1975.

Kaiser, Edward, Rohrer, Jeffrey S. and Watanabe, Kazuo, Determination of Trace Anions in Concentrated Weak Acids by Ion Chromatography, Journal of Chromatography A, 850, 1999, pp. 167–176, Elsevier Science, Amsterdam.

Vanderford, Griselda, Determination of Trace Anions in Hydrofluoric Acid by Ion Chromatography, 602, 1992, pp. 75–78, Elsevier Science, Amsterdam.

Murayama, Mitsunori, Suzuki, Masao and Takitani, Shoji, Determination of Trace Anionic Impurities in Concentrated Inorganic Acids by Recycle Ion Chromatography, 466, 1989, pp. 355–363, Elsevier Science, Amsterdam.

Mohsin, Sheher Bano, Use of Ion Chromatography—electrospray mass spectrometry for the Determination of Ionic Compounds in Agricultural Chemicals, Journal of Chromatography A, 884, 2000, pp. 23–30, Elsevier Science, Amsterdam.

Ahrer, Werner and Buchberger, Wolfgang, Analysis of Low–Molecular–Mass Inorganic and Organic Anions by Ion Chromatography–Atmospheric Pressure Ionization Mass Spectrometry, Journal of Chromatography A, 854, 1999, pp. 275–287, Elsevier Science, Amsterdam.

Buchberger, Wolfgang and Ahrer, Werner, Combination of Suppressed and Non–Suppressed Ion Chromatography with Atmospheric Pressure Ionization Mass Spectrometry for the Determination of Anions, Journal of Chromatography A, 850, 1999, pp. 99–106, Elsevier Science, Amsterdam.

Charles, L., and Pepin, D., Analysis of Oxyhalides in Water by Ion Chromatography–Ionspray Mass Spectrometry, Journal of Chromatography A, 804, 1998, pp. 105–111, Elsevier Science, Amsterdam.

Alexander, James N., Quinn, Chad J., Organic Acid Analysis by Ion Chromatography–Particle Beam Mass Spectrometry, Journal of Chromatography, 647, 1993, pp. 95–100, Elsevier Science, Amsterdam.

Seubert, A., Schminke, G., Nowak, M., Ahrer, W. and Buchberger, W., Comparison of On–Line Coupling of Ion–Chromatography with Atmospheric Pressure Ionization Mass Spectrometry and with Inductively Coupled Plasma mass Spectrometry as Tools for the Ultra–Trace Analysis of Bromate in Surface Water Samples, Journal of Chromatography A, 884, 2000, pp. 191–199, Elsevier Science, Amsterdam.

Buchberger, Wolfgang and Haider, Karl, Studies on the Combination of Ion Chromatography–Particle–Beam Mass Spectrometry with Capillary Columns, Journal of Chromatography A, 770, 1997, pp. 59–68, Elsevier Science, Amsterdam.

Villasenor, Steven R., "Heart–Cut" Column Switching Techniques for the Determination of an Aliphatic Amine in an Organic Matrix and for Low Levels of Sulfate in an Anion Matrix, Journal of Chromatography A, 671, 1994, pp. 11–14, Elsevier Science, Amsterdam.

Weir, S.I., Butler, E.C.V., Haddad, P.R., Ion Chromatography with UV Detection for the Determination of Thiosulfate and Polythionates in Saline Waters, Journal of Chromatography A, 671, 1994, pp. 197–203, Elsevier Science, Amsterdam.

Killgore, Kendall J., and Villasenor, Steven R., Systematic Approach to Generic Matrix Elimination via "heart–cut" Column–Switching Techniques, Journal of Chromatography A, 739, 1996, pp. 43–48, Elsevier Science, Amsterdam.

Medina, Hilda Ledo de, Gutierrez, Elizabeth, Colina de Vargas, Marinela, Gonzalez, Graciela, Marin, Julio and Andueza, Eduardo, Determination of Phosphate and Sulphite in Natural Waters in the Presence of High Sulphate Concentrations by Ion Chromatography Under Isocratic Conditions, Journal of Chromatography A, 739, 1996, pp. 207–215, Elsevier Science, Amsterdam.

Huang, Yuan, Mou, Shi–Fen, Liu, Ke–Na and Rivielo, J.M., Simplifies Column–Switching Technology for the Determination of Traces of Anions in the Presence of High Concentrations of Other Anions, Journal of Chromatography A, 884, 2000, pp. 53–59, Elsevier Science, Amsterdam.

Gjerde, D.T., Cox, D.J., Jandik, P. and Li, J.B., Determination of Analytes at Extreme Concentration Ratios by Gradient Ion Chromatography with Solid–Phase Reaction Detection, Journal of Chromatography, 546, 1991, pp. 151–158, Elsevier Science, Amsterdam.

Singh, Raj P., Abbas, Nureddin, M. and Smesko, Sally A., Supressed Ion Chromatographic Analysis of Anions in Environmental Waters Containing High Salt Concentrations, Journal of Chromatography A, 733; 1996, pp. 73–91, Elsevier Science, Amsterdam.

Novic, Milko, Kivjak, Blaz and Pihlar, Boris, On–Column Processes in Ion Chromatographic Determination of Nitrite and Nitrate in Heavy Mineralised Samples, Journal of Chromatography A, 827, 1998, pp. 83–89, Elsevier Science, Amsterdam.

Kaiser, Edward, Rohrer, Jeffrey S. and Jensen, Detlef, Determination of Trace Anions in High–Nitrate Matrices by Ion Chromatography, Journal of Chromatography A, 920, 2001, pp. 127–133, Elsevier Science, Amsterdam.

Siriraks, Archava, Phol, Christopher A. and Toofan, Mahmood, Determination of Trace Anions in Concentrated Acids by Means of a Moderate–Capacity Anion–Exchange Column Journal of Chromatography, 602, 1992, pp. 89–95, Elsevier Science, Amsterdam.

Charles, L., Pepin, D and Casetta, B., Electrospray Ion Chromatography–Tandem mass Spectrometry of Bromate at Sub–ppb Levels in Water, Analytical Chemistry, Aug. 1, 1996, pp. 2554–2558, vol. 68, No. 15.

Charles, L., and Pepin, D., Electrospray Ion Chromatography–Tandem Mass Spectrometry of Oxyhalides at Sub–ppb Levels, Analytical Chemistry, Jan. 15, 1998, pp. 353–359, vol. 70, No. 2.

Mohsin, Sheher Bano, Ion Chromatography Coupled with Mass Spectrometry for the Determination of Ionic Compunds in Agricultrual Chemicals, Analytical Chemistry, Aug. 15, 1999, pp. 3603–3609, vol. 71, No. 16.

Lacourse, William R., Column Liquid Chromatography: Equipment and Instrumentation, Analytical Chemistry Jun. 15, 2000, pp. 37R–51R, vol. 72, No. 12.

Burlingame, A.L., Boyd, Robert K. and Gaskell, Simon J., Mass Spectrometry, Analytical Chemistry, Jun. 15, 1996, pp. 599R–651R, vol. 68, No. 12.

Willoughby, Ross, Sheehan, Edward and Mitrovich, Samuel, A Global View of LC/MS: How to Solve Your Most Challenging Analytical Problems, Global View Publishing, Pittsburgh, Pennsylvania.

Roeder, V. and Jardy, A., Determination of Inorganic Contaminants in Concentrated Reagents by Ion Chromatography, Analusia, Mar. 1996, pp. 43–48, Elsevier, Paris, France.

Buldini, Pier Luigi, Sharma, Jawahar Lal and Sarma, Shikha, Determination of Trace Amounts of Anionic Imputities in Hydrochloric Acid by Ion Chromatography, The Analyst, Jan. 1994, pp. 121–124.

* cited by examiner

METHOD FOR THE DETERMINATION OF LOW-CONCENTRATION ANIONS IN THE PRESENCE OF AN EXCESS OF ANOTHER ANION

BACKGROUND OF THE INVENTION

1. Field of the Invention

This invention relates to the field of chromatography generally, and more specifically to the detection of anions in the presence of an excess of another anion, such as in liquids used in semiconductor manufacturing.

2. Related Art

Typical known methods of determining the presence of an anion in liquid samples use wet-chemistry procedures, which are time consuming and which typically detect and/or quantify only one analyte at a time. Some ion-chromatographic methods have been developed to address this determination, but detection has typically been by conductivity, absorbance, or amperometry.

Chromatography is the separation of mixtures of similar species (e.g., sugars, proteins, anions). In the technique, there are two "work horses": 1) a stationary phase; and 2) a mobile phase. As the names indicate, the first phase does not move but the second one does; both phases are selected because they will interact with a mixture's species (also known as analytes). Some of the analytes prefer to be in the mobile phase and thus move together out of the system rapidly; other species would rather interact with the stationary phase, moving along much more slowly. It is this difference in preferences that allows the mixture to be separated. Chromatographic systems can be designed very reproducibly, meaning that each mixture component will take a specific amount of time to move through the system. This retention time, as it is called, is the main way that substances are identified; if a sample component's retention time matches that of a known standard, then the two substances are assumed to be the same. Quantitation is achieved by measuring the responses of known concentrations of components, and comparing these numbers with sample data.

One large class of chromatographic techniques is known as liquid chromatography (LC). Here, the stationary phase is a sand-like substance called a resin, which has been treated with chemicals to establish specific separating properties. The resin is packed in a thin, cylindrical column of, typically, plastic or metal. (Although the term "column" is used herein, the skilled artisan will recognize "column" to be a generic term for any separating means.) The mobile phase is a liquid that flows through this column at all times during operation. Ion chromatography (IC) is a special type of LC. Here, the anions or cations in a mixture are separated, using specific resins and mobile phases (called eluents). The eluents usually are either bases (for anion separations) or acids (for cation samples).

The key deficiency with typical ion-chromatographic methods is that there is at least some doubt about the identity of each sample component. There may be an unknown substance that has the same retention properties as one of the analytes. In such a case, retention time alone is not sufficient to establish identification. Another detection technique, known as mass spectrometry, can help in these situations. Here, a substance is ionized so that it will break apart into fragments. The fragmentation pattern for each chemical is distinct and reproducible from one analysis to the next. These facts make mass spectrometry one of the best means of identifying a substance. (Because a mass spectrometer can help detect, identify, and quantify specific substances, it is often called a specific detector.)

Mass spectrometry can be linked with a chromatographic system like IC. The chromatography portion (i.e., the separation) is accomplished first. As the eluent exits the ion chromatograph, the liquid is directed into the spectrometer for fragmentation and identification of each component. The resulting pattern can often confirm if each substance is the same as what the retention time indicates.

One common problem in the semiconductor art and other arts is that a user of a liquid chemical would like to detect and/or quantify one or more anions, which exists in the solution in a very minor portion in a huge sea of anions of another type. For example, aqueous acidic solutions used in semiconductor manufacturing may contain very minor portions of chloride ion ($Cl^-$) in a very major portion of nitrate ions ($NO_3^-$). The same situation can occur in basic pH solutions. The problem is particularly acute in strong acid and strong basic solutions. In these situations, the strong acids and strong bases are completely dissociated, thereby providing the extremely high concentration of the major-portion anion. An example of this is aqueous hydrochloric acid (HCl), which is dissociated into positively charged hydronium ions and negatively charged chloride ions. It may be necessary or convenient to the user to know how much sulfate ion ($SO_4^{2-}$) is contained within an aqueous hydrochloric-acid solution.

A combination of liquid chromatography and mass spectrometry is presently used for the detection and/or quantification of certain species in so-called "neutral organics" such as drug compositions, protein compositions, and the like. However, it does not appear anywhere in the art known to the inventor to use a combination of ion chromatography with mass spectrometry to detect and/or quantify a very minor portion of an anion in a very major portion of another anion, particularly in weak acids, strong acids, and salts thereof.

SUMMARY OF THE INVENTION

In accordance with the present invention, methods have been designed to allow analysis (detection, quantification, and/or identification) of trace anions in strong-acid compositions, preferably comprising one or more of HCl, $HNO_3$, $H_2SO_4$, and the like, as well as in weak-acid compositions, preferably comprising one or more of $H_3PO_4$, $CH_3COOH$, HF, citric acid, boric acid, oxalic acid, trichloroacetic acid, and the like, thus providing reassurance to users of such compositions with increasingly restrictive anion specifications. The methods and apparatus of the invention may also be used for analysis of trace anions in salts of strong-acid compositions, preferably comprising $NaNO_3$, $Na_2SO_4$, NaCl, and the like, and salts of weak-acid compositions, preferably comprising $Na_3PO_4$, $CH_3COONa$, and the like.

In general, methods of the invention involve first using the ion chromatograph to separate the bulk of the excess anion from the analytes of interest. This separation is accomplished by using an ion chromatograph's anion separator (hereinafter referred to as a "separator" and defined as any means for separating anions from each other). As the analytes exit the separator, they enter a suppression device (referred to hereinafter as an "anion suppressor" and defined as any device that exchanges the eluent's cations for hydronium ions). Upon leaving the anion suppressor, the analytes are trapped on an anion-trapping means, preferably a column; when excess anions are exiting the separator, the excess anions are sent to waste by means of a switching valve. After the first separation is complete, the trapped analytes are introduced to a second separator, where they are further resolved. As the individual anions of interest exit the second separator, they are sent into a second anion suppressor, and then into a mass spectrometer (MS) for detection. If necessary, a second switching valve is used to send any remaining excess anions to waste, so they do not enter the MS.

The methods of the present invention are novel and non-obvious, and important commercially for two reasons. First, as mentioned earlier, the MS is a specific detector. Consequently, it does not require as high a degree of analyte resolution as detectors that operate on the basis of, for example, conductivity, absorbance, or amperometry. Second, the MS allows identification of the analytes; detectors that operate on conductivity, absorbance, or amperometry, for example, do not have this feature and do not operate on this basis.

A preferred process in accordance with the invention is a process for detecting trace quantities of an anion in the presence of an excess of another anion, the process comprising: (a) loading a liquid sample comprising the anion of interest and an excess of another anion onto means selected from the group consisting of an anion concentrator (referred to hereinafter as a "concentrator" and defined as any means to concentrate anions) and a sample loop by flowing the liquid sample there through in a first direction; (b) reversing the direction of flow through the concentrator or sample loop to form an eluent stream; and (c) flowing the eluent stream into a mass spectrometer adapted to accept the eluent stream, and using the mass spectrometer for detecting the anion of interest.

Preferred processes in accordance with this aspect of the invention are those wherein the anion of interest is selected from the group consisting of chloride ion, chlorite ion, chlorate ion, perchlorate ion, bromide ion, bromate ion, fluoride ion, nitrite ion, nitrate ion, sulfate ion, sulfite ion, chromate ion, iodide ion, borate ion, phosphate ion, polyphosphate ions, thiocyanate ion, thiosulfate ion, selenate ion, selenite ion, tungstate ion, arsenate ion, as well as anions of organic acids such as acetic acid, tartaric acid, phthalic acid, and the like; processes wherein the liquid sample comprises compositions selected from the group consisting of strong acids (for example aqueous hydrochloric acid, aqueous nitric acid and aqueous sulfuric acid), weak acids (such as $H_3PO_4$ and $CH_3COOH$, HF, citric acid, boric acid, oxalic acid, and trichloroacetic acid), and salts of weak acids and salts of strong acids. Further preferred are processes wherein a plurality of anions of interest are identified in a single liquid sample comprising a composition selected from the group consisting of a strong acid, a weak acid, a salt of a strong acid, and a salt of a weak acid. Particularly preferred processes in accordance with the first aspect are those wherein steps a, b, and c, are accomplished using a six-port valve.

A second aspect of the invention is an apparatus for detecting trace quantities of an anion in the presence of an excess of another anion, the apparatus comprising: (a) means for loading a liquid sample comprising the anion of interest and an excess of another anion onto a device selected from the group consisting of a concentrator and a sample loop; (b) means for reversing flow through the device creating an eluent flow; and (c) a mass spectrometer adapted to accept the eluent flow, and thereafter used to detect the anion of interest.

Particularly preferred are apparatus wherein means (a) and (b) comprise a sample-injection device and a manifold, especially wherein the manifold comprises multiple ports. Such a manifold is preferably a six-port valve that may be moved between two positions, as further described herein.

Means for loading liquid samples include a sampling pump, an auto sampler, a pressurized vessel (typically and preferably pressurized via gas), a syringe, a vacuum supplied at a convenient spot in the apparatus (typically a waste port), and combinations of these techniques.

For loading via a sampling pump, a tube is placed into the sample container, the pump is turned on, and the sample liquid is pulled out and sent (via tubing on the pump's outlet) to a load/inject valve. An alternate method is to place a sucking pump (for example, a vacuum pump) on a waste port of the load/inject valve. The pump is then turned on to suck the sample into the sample loop or concentrator.

An autosampler may be used to load the sample. The autosampler is preferably computer-controlled and accommodates multiple sample containers. Tubing extends from the sample container to the sampler, and tubing is attached to the load/inject valve. Preferably, the computer will automatically tell the sampler to load the various samples in a specific order and at specific times.

For loading via a pressurized vessel, the sample container is placed in a vessel that can be pressurized with a gas. A tube goes into the sample container, through an opening in the vessel, and to the load/inject valve. The sample is forced into the sample loop or concentrator when the vessel is pressurized.

A syringe may used to load the sample by filling a syringe and attaching tubing from the syringe to the load/inject valve. The plunger of the syringe is pushed to force the liquid into the sample loop or concentrator. An alternate method is to place the syringe on a waste port of the load/inject valve. The plunger is then pulled to suck the sample into the sample loop or the concentrator.

A third aspect of the invention is a process for detecting trace quantities of an anion of interest in the presence of an excess of another anion, in a liquid sample, the process comprising: (a) loading a liquid sample comprising the anion of interest and an excess of another anion onto a sample loop; (b) moving the liquid sample through the sample loop through a first separator, creating a first eluent stream; (c) (i) routing the stream to waste if excess anion is present and (ii) if the anion(s) of interest is (are) present, routing the first eluent stream to a first anion suppressor and creating a first anion-suppressor effluent; (d) flowing the first anion-suppressor effluent to a concentrator for trapping the anion of interest; (e) aligning the concentrator with a second separator and reversing flow through the concentrator to produce a concentrator effluent; (f) flowing the concentrator effluent through the second separator to create a second eluent stream; (g) routing the second eluent stream through a second anion suppressor and creating a second anion-suppressor effluent; and (h) routing the second anion-suppressor effluent through a mass spectrometer adapted to accept the second anion-suppressor effluent, and using the mass spectrometer for detecting the anion of interest.

Preferred are those processes in accordance with this aspect of the invention wherein prior to step (a)–(h), a portion of the liquid sample is loaded onto the sample loop and moved through the sample loop, the first separator, a third anion suppressor, and an ion detector, thereby establishing timing when the anion of interest and the excess anion will leave the first separator. Particularly preferred is a process wherein steps (a)–(h) are accomplished using four six-port valves, as further described herein, and wherein steps (a)–(h) are controlled by a computer.

A fourth aspect of the invention is an apparatus for detecting trace quantities of an anion in the presence of an excess of another anion, the apparatus comprising:

(a) a sample loop having a first end adapted to be connected to a first connection selected from the group consisting of a sample-injection device and a first pump, and a second end adapted to be connected to a second connection selected from the group consisting of an inlet of a first separator and a waste port;

(b) the first separator having an outlet connection adapted to be connected to a connection selected from the group consisting of a second waste port and an inlet of a first anion suppressor;

(c) the first anion suppressor having an inlet connection adapted to be connected to a connection selected from the group consisting of a second pump and the outlet connection of the first separator, and an outlet connection adapted to be selected from the group consisting of an inlet of a concentrator and a third waste port;

(d) the concentrator having an inlet connection adapted to be connected to a connection selected from the group consisting of an inlet of a second separator and the outlet of the first anion suppressor, and an outlet connection adapted to be selected from the group consisting of a fourth waste port or a third pump;

(e) the second separator having an inlet connection adapted to be connected to a connection selected from the group consisting of the third pump or the concentrator inlet, and an outlet connection adapted to be connected to an inlet of a second anion suppressor, the second anion suppressor having an outlet connection; and (f) the second anion-suppressor outlet connection adapted to be connected to a mass spectrometer adapted to accept an effluent from the outlet of the second anion suppressor, and thereafter used to detect the anion of interest.

A fifth aspect of the invention is a process for quantifying trace quantities of an anion in the presence of an excess of another anion, the process comprising: (a) loading a liquid sample comprising the anion of interest and an excess of another anion onto means selected from the group consisting of a concentrator and a sample loop by flowing the liquid sample there through in a first direction; (b) reversing the direction of flow through the concentrator or sample loop to form an eluent stream; and (c) flowing the eluent stream into a mass spectrometer adapted to accept the eluent stream, and using the mass spectrometer for quantifying the anion of interest.

A sixth aspect of the invention is an apparatus for quantifying trace quantities of an anion in the presence of an excess of another anion, the apparatus comprising: (a) means for loading a liquid sample comprising the anion of interest and an excess of another anion onto a device selected from the group consisting of a concentrator and a sample loop; (b) means for reversing flow through the device creating an eluent flow; and (c) a mass spectrometer adapted to accept the eluent flow, and thereafter used to quantify the anion of interest.

A seventh aspect of the invention is a process for quantifying trace quantities of an anion of interest in the presence of an excess of another anion in a liquid sample, the process comprising;

(a) loading a liquid sample comprising the anion of interest and an excess of another anion onto a sample loop;

(b) moving the liquid sample through the sample loop through a first separator, creating a first eluent stream;

(c) (i) routing the stream to waste if excess anion is present and (ii) if the anion(s) of interest is (are) present, routing the first eluent stream to a first anion suppressor and creating a first anion-suppressor effluent;

(d) flowing the first anion-suppressor effluent to a concentrator for trapping the anion of interest;

(e) aligning the concentrator with a second separator and reversing flow through the concentrator to produce a concentrator effluent;

(f) flowing the concentrator effluent through the second separator to create a second eluent stream;

(g) routing the second eluent stream through a second anion suppressor and creating a second anion-suppressor effluent; and (h) routing the second anion-suppressor effluent through a mass spectrometer adapted to accept the second anion-suppressor effluent, and using the mass spectrometer for quantifying the anion of interest.

Preferred are those processes in accordance with this aspect of the invention wherein prior to step (a)–(h), a portion of the liquid sample is loaded onto the sample loop and moved through the sample loop, the first separator, a third anion suppressor, and an ion detector, thereby establishing timing when the anion of interest and the excess anion will leave the first separator. Particularly preferred is a process wherein steps (a)–(h) are accomplished using four six-port valves, as further described herein, and wherein steps (a)–(h) are controlled by a computer.

An eighth aspect of the invention is an apparatus for quantifying trace quantities of an anion in the presence of an excess of another anion in a liquid sample, the apparatus comprising:

(a) a sample loop having a first end adapted to be connected to a first connection selected from the group consisting of a sample-injection device and a first pump, and a second end adapted to be connected to a second connection selected from the group consisting of an inlet of a first separator and a waste port;

(b) the first separator having an outlet connection adapted to be connected to a connection selected from the group consisting of a second waste port and an inlet of a first anion suppressor;

(c) the first anion suppressor having an inlet connection adapted to be connected to a connection selected from the group consisting of a second pump and the outlet connection of the first separator, and an outlet connection adapted to be selected from the group consisting of an inlet of a concentrator and a third waste port;

(d) the concentrator having an inlet connection adapted to be connected to a connection selected from the group consisting of an inlet of a second separator and the outlet of the first anion suppressor, and an outlet connection adapted to be selected from the group consisting of a fourth waste port and a third pump;

(e) the second separator having an inlet connection adapted to be connected to a connection selected from the group consisting of the third pump or the concentrator inlet, and an outlet connection adapted to be connected to an inlet of a second anion suppressor, the second anion suppressor having an outlet connection; and (f) the second anion-suppressor outlet connection adapted to be connected to a mass spectrometer adapted to accept an effluent from the outlet of the second anion suppressor, and thereafter used to quantify the anion of interest.

A ninth aspect of the invention is a process for identifying an anion in the presence of an excess of another anion, the process comprising:

(a) loading a liquid sample comprising the anion of interest and an excess of another anion onto means selected from the group consisting of a concentrator and a sample loop by flowing the liquid sample there through in a first direction;

(b) reversing the direction of flow through the means to form an eluent stream; and (c) flowing the eluent stream into a mass spectrometer adapted to accept the eluent stream, and using the mass spectrometer for identifying the anion of interest.

A tenth aspect of the invention is an apparatus for identifying trace quantities of an anion in the presence of an excess of another anion, the apparatus comprising:

(a) means for loading a liquid sample comprising the anion of interest and an excess of another anion onto a device selected from the group consisting of a concentrator and a sample loop;

(b) means for reversing flow through the device creating an eluent flow; and (c) a mass spectrometer adapted to accept the eluent flow, and thereafter used to identify the anion of interest.

An eleventh aspect of the invention is a process for identifying trace quantities of an anion of interest in the presence of an excess of another anion in a liquid sample, the process comprising;

(a) loading a liquid sample comprising the anion of interest and an excess of another anion into a sample loop;

(b) moving the liquid sample through the sample loop through a first separator, creating a first eluent stream;

(c) (i) routing the stream to waste if excess anion is present and (ii) if the anion(s) of interest is (are) present, routing the first eluent stream to a first anion suppressor and creating a first anion-suppressor effluent;

(d) flowing the first anion-suppressor effluent to a concentrator for trapping the anion of interest;

(e) aligning the concentrator with a second separator and reversing flow through the concentrator to produce a concentrator effluent;

(f) flowing the concentrator effluent through the second separator to create a second eluent stream;

(g) routing the second eluent stream through a second anion suppressor and creating a second anion-suppressor effluent; and (h) routing the second anion-suppressor effluent through a mass spectrometer adapted to accept the second anion-suppressor eluent, and using the mass spectrometer for identifying the anion of interest.

Preferred are processes in accordance with the eleventh aspect wherein prior to step (a)–(h), a portion of the liquid sample is loaded onto the sample loop and moved through the sample loop, the first separator, a third anion suppressor, and an ion detector, thereby establishing timing when the anion of interest and the excess anion will leave the first separator. Particularly preferred is a process wherein steps (a)–(h) are accomplished using four six-port valves, as further described herein, and wherein steps (a)–(h) are controlled by a computer.

A twelfth aspect of the invention is an apparatus for identifying trace quantities of an anion in the presence of an excess of another anion in sample, the apparatus comprising:

(a) a sample loop having a first end adapted to be connected to a first connection selected from the group consisting of a sample-injection device and a first pump, and a second end adapted to be connected to a second connection selected from the group consisting of an inlet of a first separator and a waste port;

(b) the first separator having an outlet connection adapted to be connected to a connection selected from the group consisting of a second waste port and an inlet of a first anion suppressor;

(c) the first anion suppressor having an inlet connection adapted to be connected to a connection selected from the group consisting of a second pump and the outlet connection of the first separator, and an outlet connection adapted to be selected from the group consisting of an inlet of a concentrator and a third waste port;

(d) the concentrator having an inlet connection adapted to be connected to a connection selected from the group consisting of an inlet of a second separator and the outlet of the first anion suppressor, and an outlet connection adapted to be selected from the group consisting of a fourth waste port and a third pump;

(e) the second separator having an inlet connection adapted to be connected to a connection selected from the group consisting of the third pump or the concentrator inlet, and an outlet connection adapted to be connected to an inlet of a second anion suppressor, the second anion suppressor having an outlet connection; and (f) the second anion-suppressor outlet connection adapted to be connected to a mass spectrometer adapted to accept an effluent from the second anion-suppressor outlet, and thereafter used to identify the anion of interest.

Preferred apparatus in accordance with the fourth, eighth and twelfth aspects are those wherein the apparatus components are adapted to be connected as explained in the description and drawing figures herein.

A further understanding of the invention will be had by reviewing the attached drawing figures, and by reading the description that follows. The drawings are not to scale and are intended to be illustrative only, and are not intended to limit the scope of the invention in any fashion.

DESCRIPTION OF PREFERRED EMBODIMENTS

For several years now, the art has been looking for possible approaches to detecting, identifying, and quantifying anions in concentrated strong acids, weak acids, salts of strong acids, and salts of weak acids by ion chromatography (IC). In the semiconductor art, presently the acids that are problematic are the strong acids (hydrochloric acid, sulfuric acid, and nitric acid). By "strong" is meant having an extremely high dissociation constant. In other words, the acid is essentially 100% dissociated (i.e., fully ionized) in water. A strong monoprotic acid that is fully ionized has a hydrogen-ion concentration equal to the original molar concentration of the acid. In strong acids, the predominant anion cannot be eliminated by ion exclusion, since that technique is suitable only for acids that are considered "weak" (i.e., only partially dissociated in water) acids; for example, acetic acid, citric acid, and the like. However, methods of the present invention are preferred even for weak acids, salts of strong acids, and salts of weak acids.

The present specifications for anions in the three strong acids currently used in semiconductor manufacturing are shown in Table I.

TABLE I

| Anion | HCl | HNO$_3$ | H$_2$SO$_4$ |
|---|---|---|---|
| Cl$^-$ | X | 50 | 50 |
| NO$_3^-$ | — | X | 100 |
| SO$_4^{2-}$ | 30 | 50 | X |
| PO$_4^{3-}$ | 50 | 50 | 100 |
| SO$_3^{2-}$ | 100 | — | — |

All specifications are in parts per billion (ppb).

For the strong acids and the ions therein, as indicated in Table I, one must conceive other methods dealing for with the huge excess of the acid's anion. In the past, people have dealt with this problem in typical fashion, such as diluting the acid (and thereby ending up with less sensitivity) or by using column-switching techniques. In both of these situations, non-specific detectors have been used. Success has been rather limited. In any event, each acid must be approached separately.

Figure 1A:
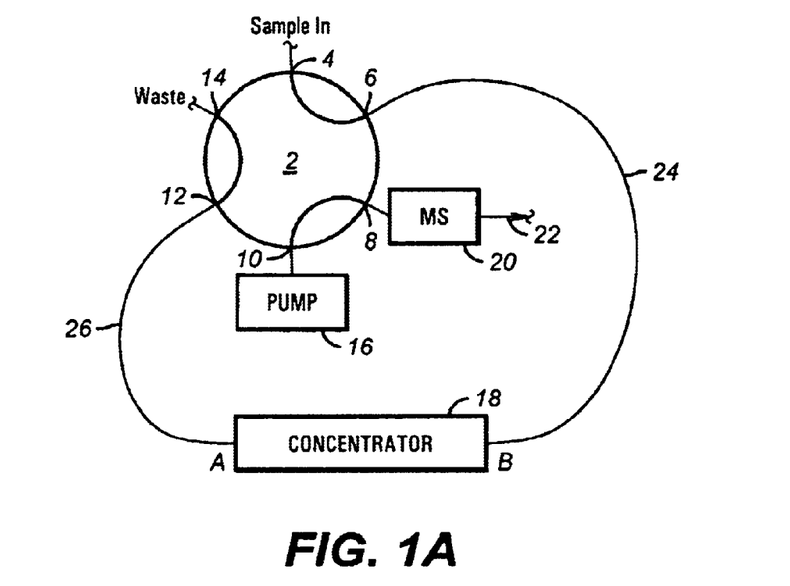
FIGS. 1A and 1B illustrate a first embodiment of the methods and apparatus in accordance with the present invention, with a variation of this embodiment illustrated in FIGS. 1C and 1D.
Figure 1B:
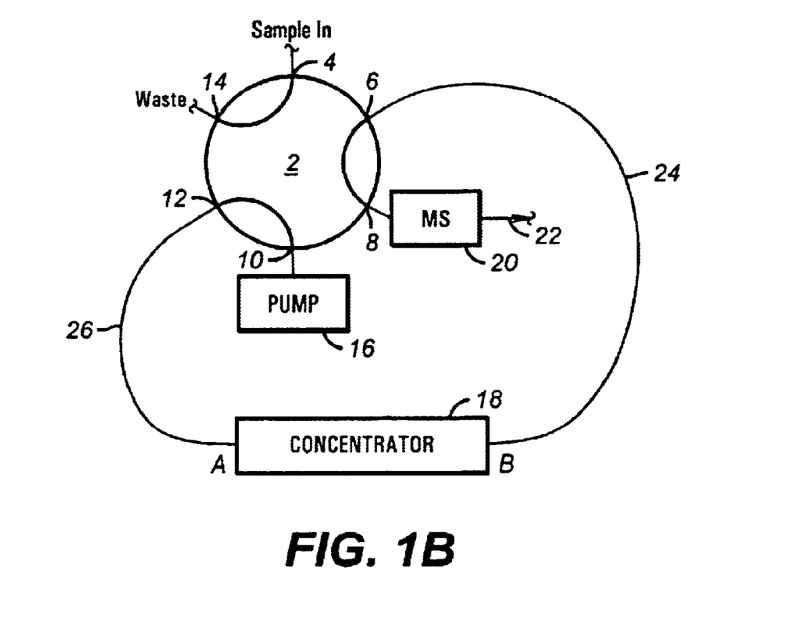

In accordance with the present invention, the inventor herein proposes to take advantage of the specificity of a mass spectrometer (MS) to help circumvent the chromatography problems. One embodiment of the invention uses a concentrator to collect all of the anions in one batch, and then introduces the batch all at once into the MS. The MS is then set to scan just the masses of the analytes of interest. FIGS. 1A and 1B illustrate this embodiment of the invention.

Referring specifically to FIG. 1A, illustrated schematically is a six-port valve 2, which has a sample-inlet port 4, port 6, whose use will be described, and a port 8 for allowing liquid flow to move through a mass spectrometer 20. Another port 10 may be used to receive fluid from a pump 16, and yet another port 12 may receive fluid flow to or from a concentrator 18 through tubing 26. A final port 14 allows liquid flow to waste. FIG. 1A illustrates the configuration of valve 2 that allows sample loading, sometimes referred to as the "load position". The sample is loaded through port 4, traverses through port 6, and through tubing 24 into a concentrator 18 in the direction from end B to end A, as illustrated in FIG. 1A. Concentrator 18 collects all the anions in a batch. Initially, liquid exiting concentrator 18 is routed to waste through tubing 26, and ports 12 and 14. Pump 16 initially pumps an eluent through port 10 and port 8 and through the mass spectrometer 20 to waste 22.

Referring now to FIG. 1B, after the sample is loaded and the anions are all concentrated in a batch on concentrator 18, valve 2 is switched so that ports 4 and 14 are aligned as well as ports 6 and 8 respectively, and ports 10 and 12 respectively. Pump 16 then pumps eluent through port 10, then port 12, then tubing 26, continuing through concentrator 18 and tubing 24. Eluent, now containing anion of interest, continues through port 6 and then port 8, and then finally onto the mass spectrometer 20 and waste 22. Ports 4 and 14 are not part of the flow path in this step.

FIGS. 1A and 1B may be summarized as in Table 2.

TABLE 2

Convention:

(a) Valve in load position
(i) Valve in inject position
Direction of Flow

Port 1 (reference numeral 6 in FIG. 1):

(a) from sample container (via port 6) to end B of concentrator 18;
(b) from end B of concentrator 18 to mass spectrometer (MS) 20, via port 2;
Port 2 (reference numeral 8 in FIG. 1):

(a) from pump 16, via port 3 to MS 20;
(b) from end B on concentrator 18, via port 1, to MS 20;
Port 3 (reference numeral 10 in FIG. 1):

(a) from pump 16 to MS 20, via port 2;
(b) from pump 16 to end A of concentrator 18, via port 4;
Port 4 (reference numeral 12 in FIG. 1):

(a) from end A of concentrator 18 to waste, via port 5;
(b) from pump 16, via port 3, to end A of concentrator 18;
Port 5 (reference numeral 14 in FIG. 1):

(a) from end A of concentrator 18, via port 4, to waste;
(b) from sample container, via port 6, to waste;
Port 6 (reference numeral 4 in FIG. 1):

(a) from sample container to end B of concentrator 18, via port 1;
(b) from sample container to waste, via port 5.

Figure 1C:
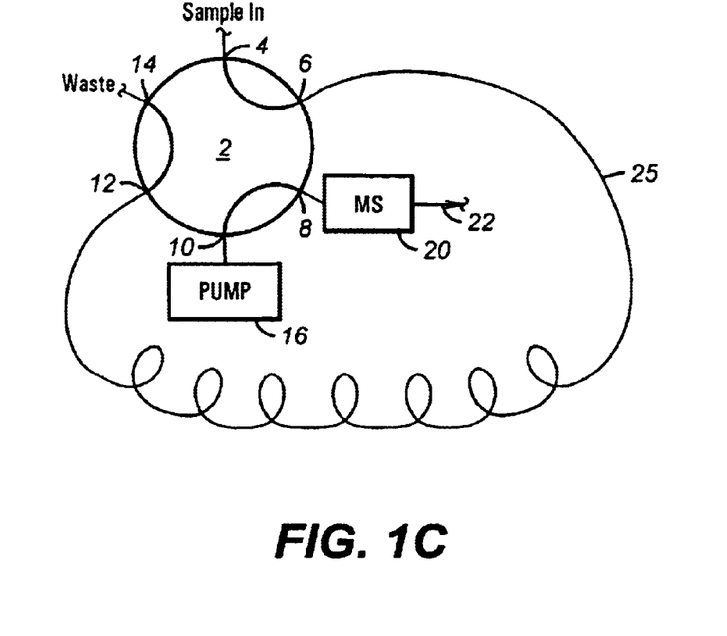
Figure 1D:
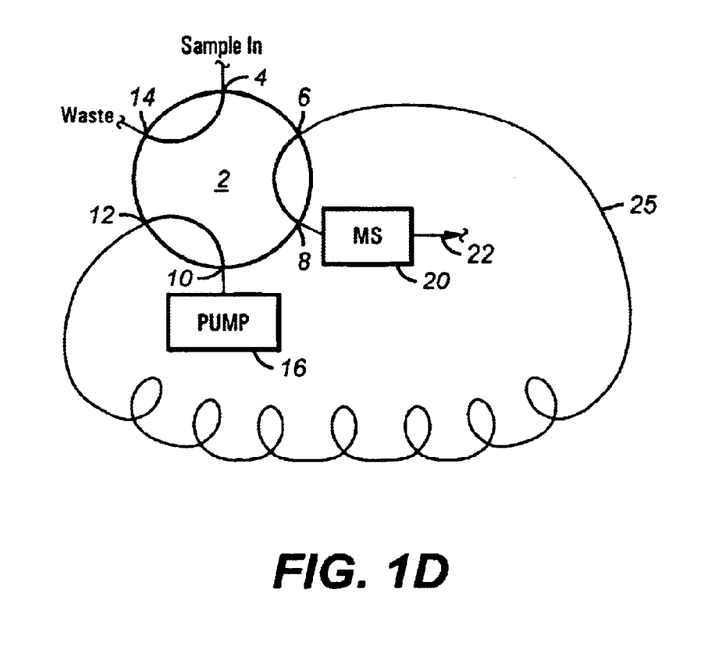

FIGS. 1C and 1D are identical to FIGS. 1A and 1B, respectively, except that conduits 24 and 26, as well as concentrator 18, are replaced by a sample loop 25. (It should be understood by those of skill in the art that when using a sample loop, the port labeled "waste" could be a "sample-inject" port and vice versa.)

One preferred mass spectrometer that is useful for the invention is a Finnegan AQA™ Mass Spectrometric Detector, which is supplied by Thermo Finnegan of Oakland, Calif. Slight modifications of the mass spectrometer to accommodate a huge presence of hydronium ion (H$_3$O$^+$) may have to be made; these changes would be preferred in practicing the embodiment of FIGS. 1A, 1B, 1C, and 1D, as well as the embodiments illustrated in FIGS. 2A, 2B, 2C, 2D, and 2E. One option would be to coat the internal walls of the mass spectrometer's inlet chamber and other internals so that corrosive products that might build up from the high concentration of hydronium ion or high concentration of excess anion will not interfere with the analysis. For example, the internals may be coated with a material known under the trade designation TEFLON™, available from DuPont. Another option that might be used in conjunction with the first embodiment may be to increase the pumping or sucking power of the internal vacuum pump associated with the MS device. Since some analytes may slough off from the internal surfaces of the MS, or as acids and their corrosion products build up, the vacuum pump may have to be modified to increase its sucking power. Also, the electronics associated with the mass spectrometer may have to be modified, if necessary (either their settings or in their actual design), to accommodate the high concentrations of hydronium ion and excess anion. Electrical compensation for the high presence of positive and negative charges may be necessary.

Concentrators, for example 18, as indicated in FIGS. 1A, 1B, 1C, and 1D, are well known in the ion-chromatography art, and are preferentially columns. These columns are typically short columns (preferably 15–50 millimeters in length) that contain the stationary phase that is identical or similar to the separator used for the analysis. The function of a concentrator is to "strip" ions from a measured volume of a relatively clean aqueous-sample matrix. This process "concentrates" the desired species, thereby leading to lower detection limits. Further understanding of use of concentrator columns in ion chromatography may be had by reading "The Use of Concentrator Columns in Ion Chromatography," Technical Note 8, Dionex Corporation, Sunnyvale, Calif., 1994, incorporated by reference herein.

A second embodiment of the method and apparatus of the invention is illustrated schematically in FIGS. 2A–2E.

Figure 2A:
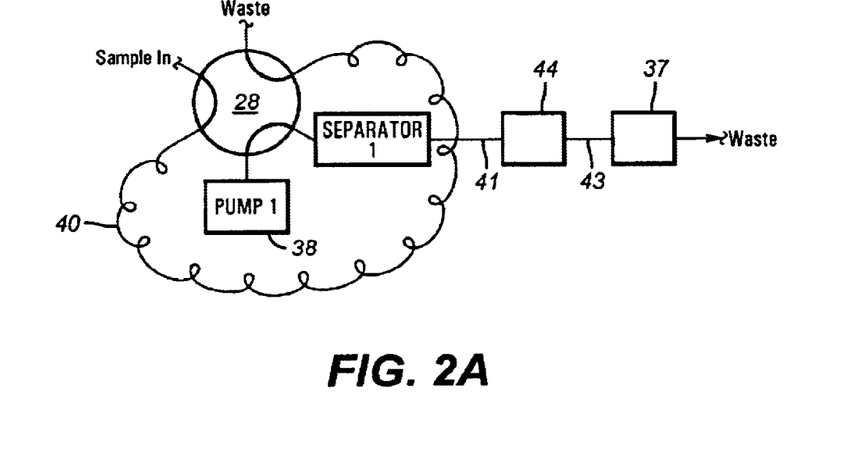
FIGS. 2A, 2B, 2C, 2D, and 2E illustrate a second embodiment of the methods and apparatus in accordance with the present invention.

FIG. 2A illustrates a technique useful for when a new sample is brought in to the laboratory for analysis, and the operator would like to know approximately when the anions of interest, and the excess anion, will elute from a given separator. Illustrated is a six-port valve 28, a sample loop 40, a first pump 38, and a first separator 36. First separator 36 is connected to an anion suppressor 44 via a conduit 41, and anion suppressor 44 is in turn connected to a detector 37 by a conduit 43. (It should be understood by those of skill in the art that when using a sample loop, the port labeled "waste" could be a "sample-inject" port and vice versa.) The operation of anion suppressors is explained herein below. Using a set-up similar to that illustrated in FIG. 2A, new samples may be used in a first apparatus to determine approximately when the anions of interest, and the excess anion, will elute from separator 36. Subsequently, as more samples of a similar nature come into the laboratory of a similar nature, operators may use the apparatus and methods of FIGS. 2B–2E, as will now be explained.

Figure 2B:
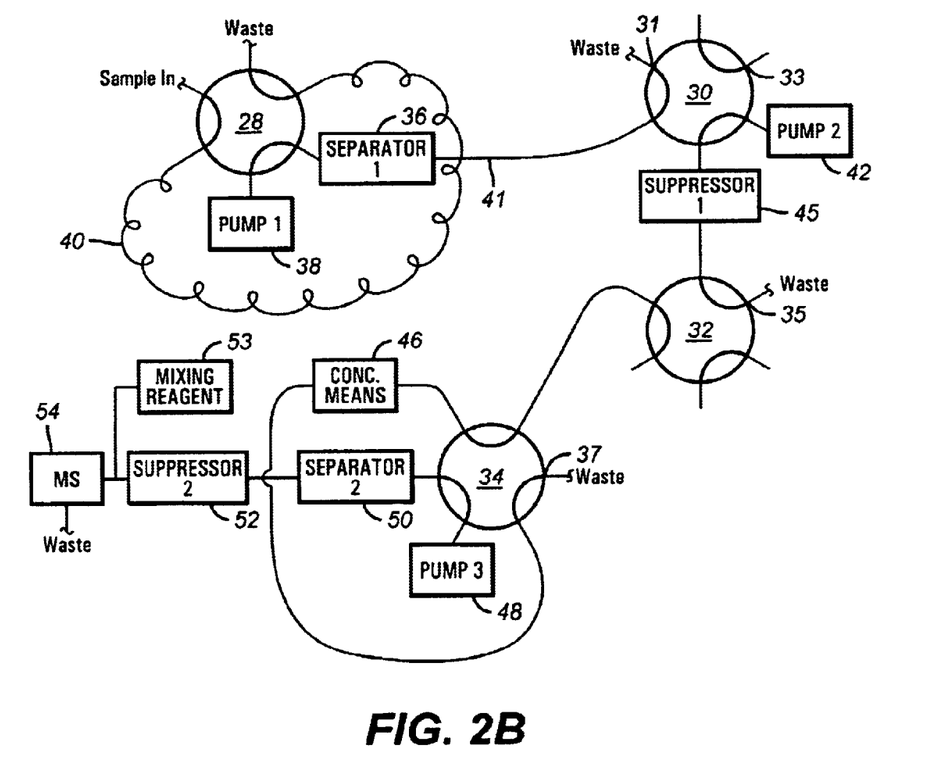

FIG. 2B illustrates schematically four different six-way valves 28, 30, 32, and 34, whose functions are further explained herein. An explanation of the settings of each port for each six-way valve is not included herewith and is assumed to be readily understood by those skilled in the art. The first six-way valve 28 accepts a sample that is loaded onto a sample loop 40. The sample might, for example, be a sample of aqueous hydrochloric-acid solution for which the sulfate anion, $SO_4^{2-}$, is an anion of interest. The sample might be loaded, for example, through a pressurized reservoir into sample loop 40. Sample loop 40 might, for example, be a 1000-microliter sample loop of tubing. Preferably, ultra pure helium or nitrogen at a given pressure above atmosphere (for example, 35 kPa (about 5 psig)) may be used to push sample from a sample container into sample loop 40 at a flow rate of about 1 milliliter per minute. This technique ensures that a representative sample of a concentrated-acid sample is loaded onto the sample loop 40. It is preferred to pass at least four loop volumes through the sample loop 40 to ensure reproducible sampling.

Figure 2C:
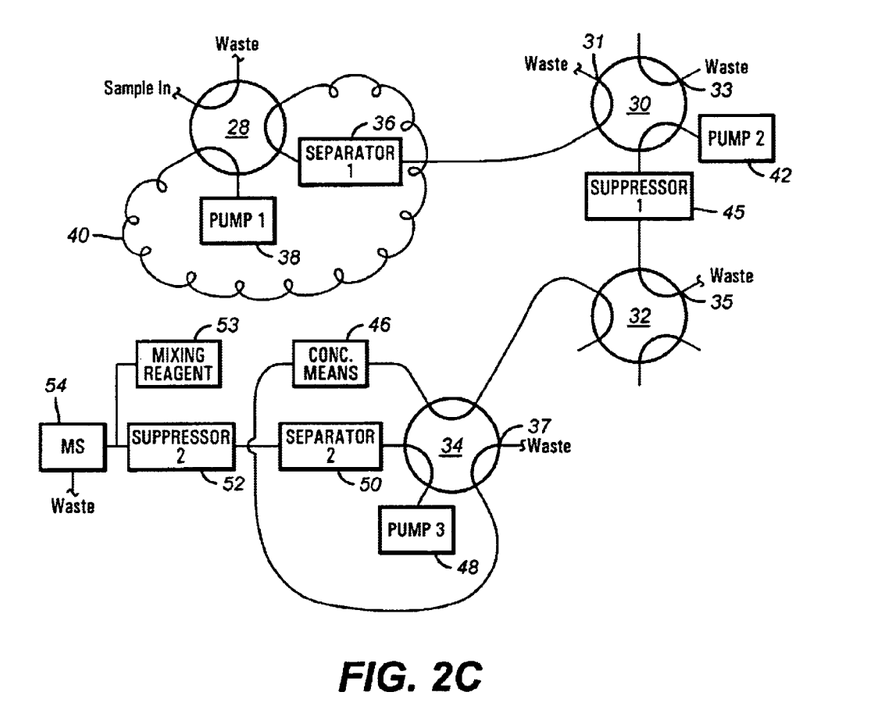

As indicated in FIG. 2C, sample is then delivered into a first separator 36, and then on to a second six-way valve 30 having waste ports 31 and 33. First separator 36 separates the various anions, allowing the bulk of the excess anion to pass to waste through waste port 31. Meanwhile, a second pump 42 pumps eluent through an anion suppressor 45, preferably an anion self-regenerating suppressor, such as available from Dionex Corporation, part number 53947 or 53946. A second anion suppressor 52 is illustrated in FIGS. 2B–2E. First and second anion suppressors may be the same or different in terms of manufacturer and part number.

Figure 2D:
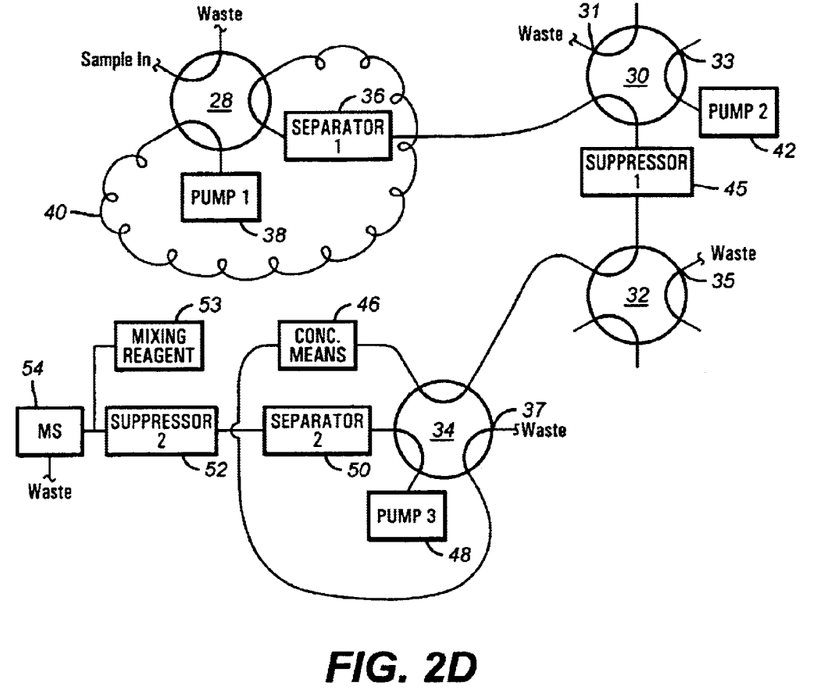

As illustrated in FIG. 2D, the eluent including anions of interest that elute either before or after the excess anion is then preferably sent through anion suppressor 45. In FIG. 2D, six-way valve 30 has one internal solid line that does not lead to waste. That line indicates that the effluent from first separator 36 is routed through first anion suppressor 45, through third six-way valve 32 and fourth six-way valve 34 and onto a concentrator 46, where anions of interest are concentrated. Eluent now substantially devoid of anions of interest passes through six-way valve 34 and out to waste at port 37.

Figure 2E:
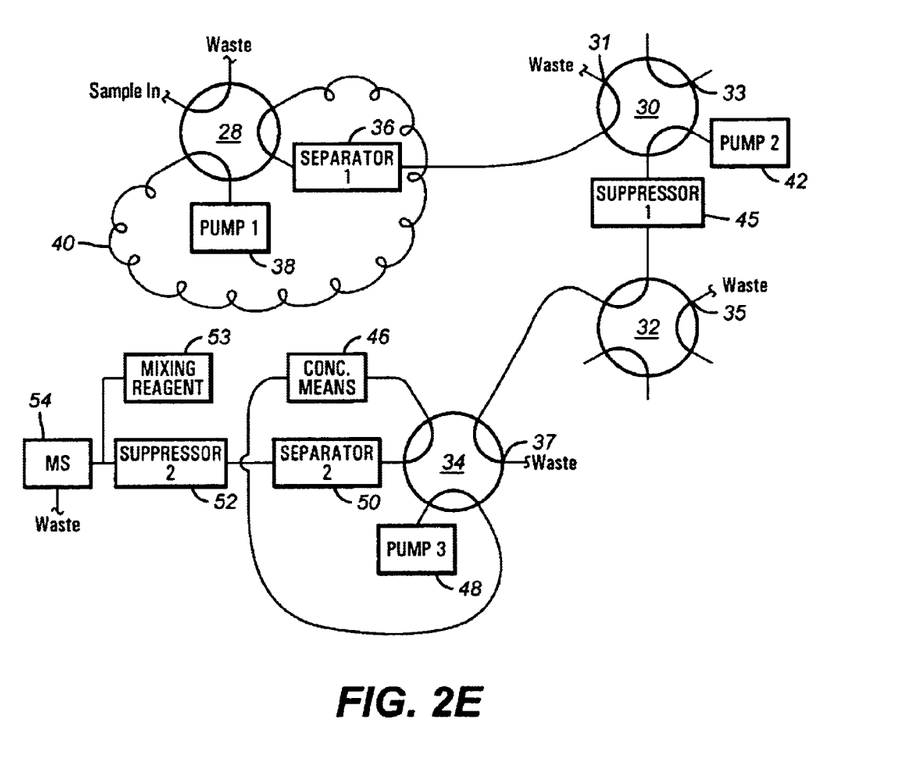

Once substantially all anions of interest are collected on concentrator 46, valves 30 and 34 are switched to the positions indicated in FIG. 2E, and concentrator 46 is placed in line with a second separator 50, for actual analysis of the anions. Pump 48 forces eluent through valve 34, concentrator 46, back through valve 34, and to second separator 50. The eluent then passes through second anion suppressor 52, and then through a mass spectrometer 54 and ultimately to waste.

Mixing reagents may optionally be added to the eluent as it flows from second anion suppressor 52 to mass spectrometer 54. This addition is indicated in FIGS. 2B–2E at 53. Mixing reagents function to allow the mass spectrometer to experience a friendlier working environment. Mixing reagents may be comprised of organic and inorganic ingredients. A non-complete list might include solvents such as alcohols, water, and buffers (such as acetate buffers) and mixtures thereof.

The protocol indicated in FIGS. 2B–2E eliminates much of the predominant anion and provides a cleaner, focused matrix for introduction onto the second separator 50. Trapping the anions of interest after the first separator 36 reconcentrates and refocuses the anions, thereby improving the sensitivity of the method. Background anion suppression is preferred first, because the ions will trap onto concentrator 46 only if they are essentially in a water matrix. The anion suppressor essentially changes the mobile phase, typically and preferably comprising an aqueous solution of base, to water. A detailed discussion of anion suppressor operation may be found in "Installation Instructions and Troubleshooting Guide for the Anion Self-Regenerating Suppressor-Ultra", Doc. 031367, Dionex Corporation, Oct. 19, 1999, which is incorporated by reference herein.

The above embodiments are not exclusive of other variations, which may become apparent to those skilled in the art. The inventor herein has utilized the specificity of a mass spectrometer to circumvent problems and deficiencies with chromatography. There may always be an unknown substance that has the same retention properties as one of the analytes in a chromatography scheme. In such a case, retention time alone is not sufficient to establish identification of an analyte. The coupling of ion chromatography with mass spectrometry can help these situations. In these situations, a substance is ionized so that it will break apart into fragments; the fragmentation pattern for each chemical is distinct and also is reproducible from one analysis to the next. These facts make mass spectrometry one of the best means of identifying a substance conclusively. The present invention links a chromatographic system, ion chromatography (IC), with mass spectrometry. The chromatography portion is accomplished first. As the eluent exits the final separator, the liquid is directed onto the mass spectrometer for fragmentation and identification of each component. The resulting pattern can help confirm if each substance is the same as what the retention time indicates.

Preferred apparatus and processes for practicing the present invention have been described. It will be understood and readily apparent to the skilled artisan that many changes and modifications may be made to the above-described embodiments without departing from the scope of the present invention. The foregoing is illustrative only, and other embodiments of the processes and apparatus may be employed without departing from the scope of the invention defined in the following claims.

What is claimed is:

1. A process for detecting trace quantities of an anion in the presence of an excess of another anion in a liquid sample, the process comprising:
    (a) loading a liquid sample comprising the anion of interest and an excess of another anion onto means selected from the group consisting of a concentrator and a sample loop by flowing the liquid sample there through in a first direction;
    (b) reversing the direction of flow through the means to form an eluent stream; and
    (c) flowing the eluent stream into a mass spectrometer adapted to accept said eluent, and using the mass spectrometer for detecting anion of interest,
wherein the liquid sample is selected from the group consisting of strong acids, and salts of strong acids, and wherein said means does not include ion exclusion.

2. Process in accordance with claim 1 wherein the anion of interest is selected from the group consisting of chloride ion, chlorite ion, chlorate ion, perchlorate ion, bromide ion, bromate ion, fluoride ion, nitrite ion, nitrate ion, sulfate ion, sulfite ion, chromate ion, iodide ion, borate ion, phosphate ion, polyphosphate ions, thiocyanate ion, thiosulfate ion, selenate ion, selenite ion, tungstate ion, arsenate ion, and anions of organic acids.

3. Process in accordance with claim 1 wherein a plurality of anions of interest are identified in a single liquid sample.

4. Process in accordance with claim 1 wherein steps a, b, and c, are accomplished using a six-port valve.

5. An apparatus for detecting trace quantities of an anion in the presence of an excess of another anion in a liquid sample, the apparatus comprising:
    (a) means for loading a liquid sample comprising the anion of interest and an excess of another anion onto a device selected from the group consisting of a concentrator and a sample loop;
    (b) means for reversing flow through said device, thereby creating an eluent flow; and
    (c) a mass spectrometer adapted to accept said eluent flow, and thereafter used to detect said anion of interest,
wherein the liquid sample is selected from the group consisting of strong acids, and salts of strong acids, and wherein said apparatus does not include ion exclusion.

6. Apparatus in accordance with claim 5 wherein said means for loading is selected from the group consisting of a pump, an autosampler, a pressurized vessel, a syringe, a vacuum applied at an exit end of the concentrator or sample loop, and combinations thereof, and said means for reversing comprises a manifold.

7. Apparatus in accordance with claim 6 wherein said manifold comprises multiple ports.

8. Apparatus in accordance with claim 7 wherein said manifold is a six-port valve that may be moved between two positions; wherein a first port directs sample flow between the concentrator and a waste port; a second port directs flow either of said sample to said concentrator, or from said concentrator to said mass spectrometer; a third port directs flow of liquids either from the pump or from the concentrator to the mass spectrometer; a fourth port directs flow either to the mass spectrometer or the concentrator; a fifth port directs flow to waste or to the concentrator; and a sixth port directs flow to waste, either from the sample container or from the concentrator.

9. A process for quantifying trace quantities of an anion in the presence of an excess of another anion in a liquid sample, the process comprising:
    (a) loading a liquid sample comprising the anion of interest and an excess of another anion onto means selected from the group consisting of a concentrator and a sample loop by flowing the liquid sample there through in a first direction;
    (b) reversing the direction of flow through said means to form an eluent stream; and
    (c) flowing the eluent stream into a mass spectrometer adapted to accept the eluent stream, and using the mass spectrometer for quantifying the anion of interest,
wherein the liquid sample is selected from the group consisting of strong acids, and salts of strong acids, and wherein said process does not include ion exclusion.

10. An apparatus for quantifying trace quantities of an anion in the presence of an excess of another anion in a liquid sample, the apparatus comprising:
    (a) means for loading a liquid sample comprising the anion of interest and an excess of another anion onto a device selected form the group consisting of a concentrator and a sample loop;
    (b) means for reversing flow through said device and creating an eluent flow; and
    (c) a mass spectrometer adapted to accept said eluent flow, and thereafter used to quantify said anion of interest,
wherein the liquid sample is selected from the group consisting of strong acids, and salts of strong acids, and wherein said apparatus does not include ion exclusion.

11. A process for identifying an anion in the presence of an excess of another anion in a liquid sample, the process comprising:
    (a) loading a liquid sample comprising the anion of interest and an excess of another anion onto means selected from the group consisting of a concentrator and a sample loop by flowing the liquid sample there through in a first direction;
    (b) reversing the direction of flow through said means to form an eluent stream; and
    (c) flowing the eluent stream into a mass spectrometer adapted to accept said eluent stream, and using the mass spectrometer for identifying the anion of interest,
wherein the liquid sample is selected from the group consisting of strong acids, and salts of strong acids, and wherein said process does not include ion exclusion.

12. An apparatus for identifying trace quantities of an anion in the presence of an excess of another anion in a liquid sample, the apparatus comprising:
    (a) means for loading a liquid sample comprising the anion of interest and an excess of another anion onto a device selected from the group consisting of a concentrator and a sample loop;
    (b) means for reversing flow through said device and creating an eluent flow; and
    (c) a mass spectrometer adapted to accept said eluent flow, and thereafter used to identify said anion of interest,
wherein the liquid sample is selected from the group consisting of strong acids, and salts of strong acids, and wherein said apparatus does not include ion exclusion.

* * * * *